United States Patent [19]

Karrer et al.

[11] 4,094,993
[45] June 13, 1978

[54] ETHERS

[75] Inventors: Friedrich Karrer, Zofingen; Saleem Farooq, Aesch, both of Switzerland

[73] Assignee: Ciba-Geigy Corporation, Ardsley, N.Y.

[21] Appl. No.: 715,353

[22] Filed: Aug. 18, 1976

[30] Foreign Application Priority Data

Aug. 26, 1975 Switzerland .................. 11036/75
Jul. 20, 1976 Switzerland .................... 9281/76

[51] Int. Cl.² ............... A01N 9/12; C07C 149/32
[52] U.S. Cl. ............................ 424/337; 260/609 F
[58] Field of Search ................ 260/609 F; 424/337

[56] References Cited

U.S. PATENT DOCUMENTS 3,240,703  3/1966  Symon et al. .................. 260/609 F

FOREIGN PATENT DOCUMENTS 2,304,962  1974  Switzerland .................... 260/609 F

*Primary Examiner*—Delbert R. Phillips
*Attorney, Agent, or Firm*—Harry Falber

[57] ABSTRACT

New ethers of the formula

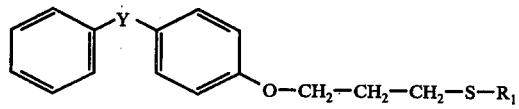

are disclosed, wherein $R_1$ represents an alkyl group having 1 to 4 carbon atoms and Y represents an oxygen or sulphur atom. These compounds are useful as pesticides, especially for the control of insects and pests of the order Acarina. The compounds are also useful for combating ectoparasites which affect livestock and domestic animals.

1 Claim, No Drawings

ETHERS

The present invention provides new diethers, a process for their manufacture and a method of using them in pest control.

The diethers of this invention have the formula I

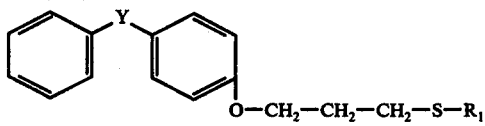

wherein $R_1$ represents an alkyl group having 1 to 4 carbon atoms and Y represents an oxygen or sulphur atom.

Possible alkyl groups represented by $R_1$ are methyl, ethyl, propyl, isopropyl, n-butyl, iso-butyl, sec. and tert.butyl. Preferred compounds on account of their activity are those of the formula I, wherein Y represents an oxygen atom. The compounds of the formula I can be prepared by methods which are known per se:

A)

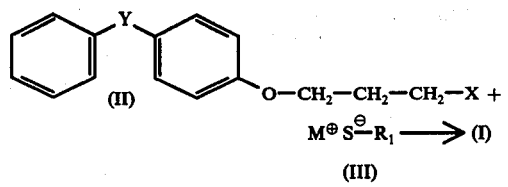

B)

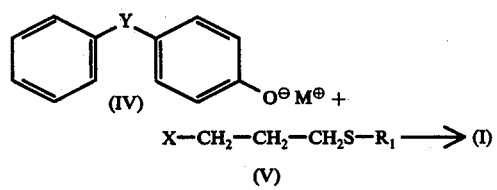

C)

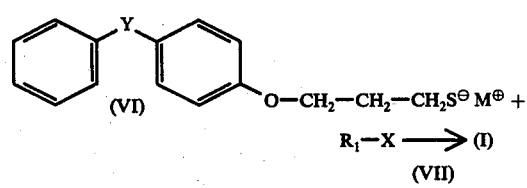

In the formulae II to VII, the symbols $R_1$ and $Y_1$ are as defined in formula I, X represents halogen, in particular a chlorine or bromine atom and M is a metal of groups 1 and 2 of the Periodic Table, in particular sodium, potassium or lithium. The above processes A, B and C are carried out at a reaction temperature of 10° to 120° C (processes A and C at a temperature of 10° to 80° C, preferably 20° to 60° C, and process B at a temperature of 20° to 120° C, preferably 20° to 100° C), at normal pressure and in the presence of inert solvents or diluents.

Suitable solvents or diluents are preferably: dimethyl sulphoxide, dimethyl formamide, hexamethylphosphoric triamide; ethers, such as dimethoxyethane, dioxane, tetrahydrofurane; and ketones, such as acetone, methyl ethyl ketone, cyclohexanone; and also water or mixtures of these solvents.

The starting materials of the formulae II to VII are known compounds or they can be prepared in analogous manner to known methods which are described in the literature.

The compounds of formula I are suitable for the control of a variety of animal and plant pests, particularly for combating members of the order Acarina of the families: Ixodidae, Argasidae, Tetranychidae, Dermanyssidae, and insects of the families: Acrididae, Blattidae, Gryllidae, Gryllotalpidae, Terrigoniidae, Cimicidae, Pyrrhocoridae, Reduviidae, Aphididae, Delphacidae, Diaphididae, Pseudococoidae, Chrysomilidae, Coccinellidae, Bruchidae, Scarabaeidae, Dermestidae, Tenebrionidae, Curculionidae, Tineidae, Noctuidae, Lymantridae, Pyralidae, Galleridae, Culicidae, Tipulidae, Stomoxydae, Muscidae, Galliphoridae, Trypetidae, Pulicidae.

The compounds of the formula I are furthermore suitable for controlling ectoparasites in domestic animals and productive livestock, for example by treating animals, cowsheds, stables, barns, etc., and meadows. The ectoparasites which can be controlled with the aid of the compounds of the present invention of the formula I, or of compositions which contain these compounds, include representatives of the order Acarina, in particular parasitic ticks and mites of the families: Ioxodidae, Argasidae, Sarcoptidae, Psoroptidae, Dermanyssidae and Demodicidae, and insects affecting productive livestock and domestic animals of the orders Diptera, in particular of the families: Muscidae, Calliphoridae, Oestridae and Hippoboscidae, and of the orders Mallophaga, Amaplura and Siphonaptera.

The insecticidal action of the compounds of the formula I can be substantially broadened and adjusted to prevailing conditions by adding other insecticides or acaricides.

Examples of suitable additives are: organic phoshorus compounds, nitrophenols and their derivatives; formamidines, ureas, carbamates, chyrsanthemum acid derivatives or chlorinated hydrocarbons.

The compounds of formula I can be used as pure active substance or together with suitable carriers and/or additives. Suitable carriers or additives may be solid or liquid and correspond to the substances conventionally used in the art of formulation, for example: natural and regenerated substances, solvents, dispersing agents, wetting agents, stickers, thickeners, binders or fertilizers.

For application, the compounds of formula I can be processed to dusts, emulsion concentrates, granulates, dispersions, sprays, to solutions or suspensions in formulations well known to those skilled in the art of application.

The compositions of the present invention are obtained in known manner by intimately mixing and/or grinding active substances of formula I with suitable carriers, with or without the addition of dispersants or solvents which are inert to the active ingredients. The active substances can be applied in the following application forms.

Solid preparations: dusts, tracking agents, granulates (coated granulates, impregnated granulates and homogranulates);

Liquid preparations:

a. water-dispersible active substance concentrates: wettable powders, pastes or emulsion;

b. solutions.

The content of active substance in the compositions described above is between 0.1 and 95 percent by weight.

The active substances of formula I can be formulated for example in the following way:

Dusts:

The following substances are used for the preparation of a) a 5% b) a 2% dust:

a)
5 parts of active substance
95 parts of talcum b)
2 parts of active substance
1 part of highly dispersed silicic acid
97 parts of talcum The active ingredients are mixed and ground with the carriers.

Granulates:

The following substances are used to obtain a 5% granulate:
5 parts of active substance
0.25 parts of epichlorohydrin
0.25 parts of cetyl polyglycol ether
3.50 parts of polyethylene glycol
91 parts of kaolin (particle size 0.3–0.8 mm).

The active substance is mixed with epichlorohydrin and dissolved in 6 parts of acetone, then the polyethylene glycol and cetyl polyglycol ether are added. The resultant solution is sprayed onto kaolin and the acetone is subsequently evaporated in vacuo.

Wettable Powder

The following ingredients are used to prepare: (a) a 40%, (b) and (c) a 25% and (d) a 10% wettable powder.

(a)
40 parts of active substance,
5 parts of sodium lignin sulphonate,
1 part of sodium dibutyl-naphthalenesulphonate,
54 parts of silicic acid;

(b)
25 parts of active substance,
4.5 parts of calcium lignin sulphonate,
1.9 parts of Champagne chalk/hydroxyethyl cellulose mixture (1:1),
1.5 parts of sodium dibutyl naphthalenesulphonate,
19.5 parts of silicic acid,
19.5 parts of Champagne chalk,
28.1 parts of kaolin;

(c)
25 parts of active substance,
2.5 parts of isooctylphenoxy-polyoxyethyleneethanol,
1.7 parts of Champagne/chalk/hydroxyethyl cellulose mixture (1:1),
8.3 parts of sodium aluminum silicate,
16.5 parts of infusorial earth, (d)
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in appropriate mills and rollers. Wettable powders are obtained which can be diluted with water to give suspensions of any desired concentration.

Emulsifiable concentrates:

The following substances are used to produce (a) a 10%, (b) a 25% and (c) a 50% concentrate:

(a)
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethyl formamide,
43.2 parts of xylene;

(b)
25 parts of active substance,
2.5 parts of epoxidised vegetable oil,
10 parts of alkylarylsulphonate/fatty alcohol polyglycol ether mixture,
5 parts of dimethyl formamide,
57.5 parts of xylene;

(c)
50 parts of active substance,
4.2 parts of tributylphenol-polyglycol ether,
5.8 parts of calcium-dodecylbenzenesulphonate,
20 parts of cyclohexanone,
20 parts of xylene.

By diluting these concentrates with water it is possible to obtain emulsions of any required concentration.

Spray:

The following ingredients are used to prepare (a) a 5% spray, and (b) a 95% spray:

(a)
5 parts of active substance,
1 part of epichlorohydrin,
94 parts of ligroin (boiling range 160°–190° C);

(b)
95 parts of active substance,
5 parts of epichlorohydrin.

The invention is further illustrated by the following Examples.

EXAMPLE 1

Preparation of 1-(4-phenoxy)-phenoxy-3-ethylthio-propane

A dispersion of sodium hydride in mineral oil (4 g) is charged into a sulphonating flask, washed repeatedly with hexane, thereafter covered with a layer of 50 ml of anhydrous dimethyl sulphoxide and the bath is then cooled to 80° C. With stirring, 12.4 g of ethyl mercaptan are then added dropwise at approx. 8° to 10° C in the course of approx. 30 minutes, whereupon the sodium ethyl mercaptide which partially forms precipitates as solid phase. A solution of 30.7 g of 1-(4-phenoxy)-phenoxy-3-bromo-propane in 100 ml of dimethyl sulphoxide is subsequently added dropwise at 10° C in the course of approx. 1 hour. The reaction mixture is stirred for a further 14 hours at room temperature, then poured onto ice-water and extracted repeatedly with diethyl ether. The combined organic phases are washed repeatedly with water and a saturated solution of sodium chloride, dried over sodium sulphate and the solvent is then distilled off. The oily residue can be further purified by chromatographing it through silica gel using a mixture of ether/hexane in the ratio 1:9 as eluant, to yield pure 1-(4-phenoxy-3-ethylthio-propane; $n_D^{22}$: 1.5700.

The following compounds of the formula I are prepared in analogous manner:

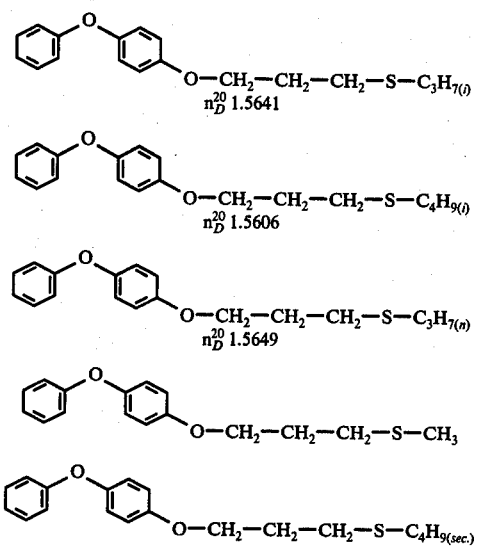

$n_D^{20}$ 1.5641

$n_D^{20}$ 1.5606

$n_D^{20}$ 1.5649

$n_D^{20}$ 1.5541 (no

EXAMPLE 2

Preparation of 1-(4-phenylmercapto)-phenoxy-3-isopropylthiopropane

To a solution of 2.58 g (0.06 mole) of potassium hydroxide in 80 ml of dimethyl formamide are added dropwise 3.5 g (0.046 mole) of isopropyl mercaptan. Then 15 g (0.046 mole) of 1-(4-phenylmercapto-phenoxy)-propyl bromide are added dropwise to this clear solution and the mixture is stirred for 4 hours at room temperature. The reaction solution is worked up by pouring it onto water and extracting it with ether. The ethereal phase is washed twice with 10% potassium hydroxide solution and subsequently three times with a saturated solution of sodium chloride. The ethereal phase is dried over sodium sulphate and the solvent is then distilled off in vacuo to yield 1-(4-phenylmercapto)-phenoxy-3-isopropylthio-propane with a refractive index of $n_D^{20}$= 1.5981.

The following compounds of the formula I are also obtained in analogous manner:

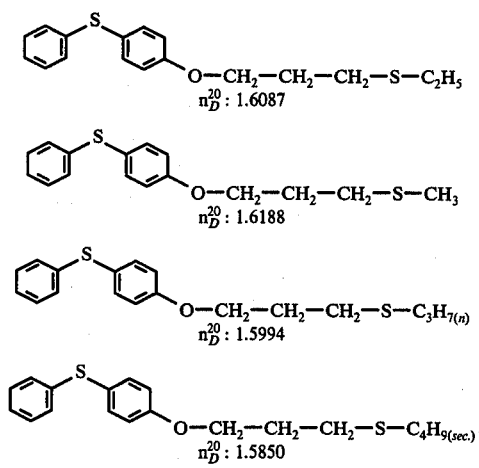

$n_D^{20}$: 1.6087

$n_D^{20}$: 1.6188

$n_D^{20}$: 1.5994

$n_D^{20}$: 1.5850

EXAMPLE 3

A. Contact action on Dysdercus fasciatus larvae

A specific amount of a 0.1% solution of active compound in acetone (corresponding to 10 mg active substance/m²) was pipetted into an aluminium dish and distributed homogeneously.

After evaporation of the acetone, 10 larvae of Dysdercus fasciatus in the fifth stage were put into the dishes containing feed and moist cotton wool. The dish was then covered with a perforated top.

After about 10 days, i.e. after the untreated controls has shed and emerged fully to the adult stage, the treated test subjects were examined for the number of normal adults.

The compounds of formula I displayed good activity in the above test.

B. Contact action on Tenebrio molitor pupae

A specific amount of a 0.1% solution of active substance in acetone, corresponding to 10 mg active substance/m², was pipetted into an aluminum dish and homogeneously dispersed.

After evaporation of the aceteone, 10 pupae which had just shed their cocoon were placed onto the treated plate. The dish was covered with a perforated top.

After the untreated controls had emerged from the pupae cocoon as imagines, the test subjects were examined for the number of adults.

The compounds of formula I showed good activity in the above test.

EXAMPLE 4

Action on ticks

A. Rhipicephalus bursa 5 adult ticks and 50 tick larvae were counted into each of a number of test tubes and immersed for 1 to 2 minutes in 2 ml of an aqueous emulsion containing a concentration of 100, 10, 1 or 0.1 ppm of test substance of formula I. The tube was then sealed with a cotton wool plug and placed on its head to enable the cotton wool to absorb the emulsion of the active substance.

The adults were evaluated after 2 weeks and the larvae after 2 days. Each test was repeated twice.

B. Boophilus microplus (larvae)

20 sensitive and 20 OP-resistant larvae were tested in a dilution series analogous to the one used in test A. (the resistance refers to the tolerance towards diazinone).

The substances of formula I acted on these tests on adults and larvae of Rhipicephalus bursa and OP-sensitive and OP-resistant larvae of Boophilus microplus.

EXAMPLE 5

Action on eggs of Spodoptera littoralis

Eggs of Spodoptera littoralis were immersed in a 0.05% solution of active compound in acetone. The treated eggs were then kept in plastic dishes at 21° C and 60% relative humidity. After 3 to 4 days the hatching out rate was determined. Compounds of formula I acted well on eggs of Spodoptera littoralis in this test.

EXAMPLE 6

Action on Musca domestica 50 g of freshly prepared CSMA nutrient substrate for maggots were charged into beakers. A specific amount of a 1% acetonic solution of the respective active substance was pipetted onto the nutrient substrate present in the beakers. The substrate was then thoroughly mixed and the acetone subsequently allowed to evaporate over a period of at least 20 hours.

Then 25 one day-old maggots of Musca domestica were put into each of the beakers containing the treated nutrient substrate for testing with each active substance at one of its given concentrations. After the maggots had pupated, the pupae were separated from the substrate by flushing them out with water and then deposited in containers closed with a perforated top.

Each batch of flushed out pupae was counted to determine the toxic effect of the active substance on the maggot development. The number of files which had hatched out of the pupae was then counted after 10 days and any influence on the metamorphosis thereby determined.

The compounds of the formula I displayed good activity in this test.

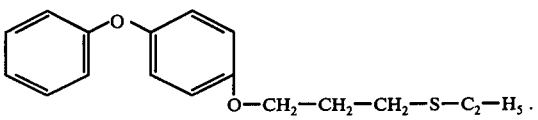

What is claimed is:

1. A method for the combatting insects and acarids which comprises applying to the locus thereof an insecticidally and acaricidally effective amount of a compound of the formula